(12) United States Patent
Uhlemann

(10) Patent No.: US 11,694,790 B2
(45) Date of Patent: Jul. 4, 2023

(54) MATCHING A SUBJECT TO RESOURCES

(71) Applicant: KONINKLIJKE PHILIPS N.V., Eindhoven (NL)

(72) Inventor: Falk Uhlemann, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 388 days.

(21) Appl. No.: 16/758,907

(22) PCT Filed: Oct. 30, 2018

(86) PCT No.: PCT/EP2018/079617
§ 371 (c)(1),
(2) Date: Apr. 24, 2020

(87) PCT Pub. No.: WO2019/086399
PCT Pub. Date: May 9, 2019

(65) Prior Publication Data
US 2021/0182599 A1 Jun. 17, 2021

(30) Foreign Application Priority Data
Oct. 30, 2017 (EP) .................................... 17199110

(51) Int. Cl.
*G16H 40/20* (2018.01)
*G06N 20/00* (2019.01)
*G06F 18/24* (2023.01)
*G06F 18/21* (2023.01)
*G06F 18/2413* (2023.01)

(52) U.S. Cl.
CPC ......... *G16H 40/20* (2018.01); *G06F 18/2178* (2023.01); *G06F 18/2413* (2023.01); *G06F 18/24765* (2023.01); *G06N 20/00* (2019.01)

(58) Field of Classification Search
None
See application file for complete search history.

(56) References Cited

U.S. PATENT DOCUMENTS

| | | | |
|---|---|---|---|
| 6,397,205 B1 * | 5/2002 | Juola | G06F 16/35 |
| 8,583,467 B1 | 11/2013 | Keane et al. | |
| 8,856,156 B1 * | 10/2014 | McNair | G06F 16/285 |
| | | | 707/602 |
| 10,198,499 B1 * | 2/2019 | McNair | G06F 16/288 |

(Continued)

FOREIGN PATENT DOCUMENTS

| | | | | |
|---|---|---|---|---|
| CN | 109416695 A | * | 3/2019 | ......... G06F 16/3329 |
| WO | 2015009550 A1 | | 1/2015 | |

OTHER PUBLICATIONS

International Search Report for PCT/EP2018/079617 dated Oct. 30, 2018.

*Primary Examiner* — Mohammed Rachedine

(57) ABSTRACT

Presented are concepts for matching a subject to one or more resources or workflow steps. Once such concept comprises obtaining data associated with a subject, the data comprising, for each of a plurality of parameters, a parameter value relating to the subject. A plurality of data groups for characterising the subject is then generated and a classification process is applied to each data group so as to generate a classification result for each data group. The subject is then matched to one or more resources or workflow steps based on the classification results.

17 Claims, 5 Drawing Sheets

(56) References Cited

U.S. PATENT DOCUMENTS

| | | |
|---|---|---|
| 2011/0082824 A1* | 4/2011 | Allison .................. G06Q 10/10 |
| | | 706/46 |
| 2011/0313790 A1 | 12/2011 | Yao |
| 2012/0173259 A1* | 7/2012 | Amberg ........... G06Q 10/06314 |
| | | 705/2 |
| 2014/0114671 A1 | 4/2014 | Hu |
| 2015/0073943 A1 | 3/2015 | Calvert et al. |
| 2015/0081326 A1 | 3/2015 | Krishnapuram et al. |
| 2015/0149212 A1 | 5/2015 | Basu et al. |
| 2015/0216436 A1* | 8/2015 | Bosl ..................... A61B 5/7275 |
| | | 600/544 |

* cited by examiner

MATCHING A SUBJECT TO RESOURCES

CROSS-REFERENCE TO PRIOR APPLICATIONS

This application is the U.S. National Phase application under 35 U.S.C. § 371 of International Application No. PCT/EP2018/079617, filed on Oct. 30, 2018, which claims the benefit of European Patent Application No. 17199110.2, filed on Oct. 30, 2017. These applications are hereby incorporated by reference herein.

FIELD OF THE INVENTION

This invention relates to the field of resource allocation and more particularly to matching a subject (such as a patient) to resources (such as medical or clinical resources for example).

BACKGROUND OF THE INVENTION

The optimization of resource utilization and workflow based on specific characteristics of a subject is a widely known problem. However, the degree to which data is available for such a problem has increased dramatically over the last years. For example, the degree of investigation and standardization of medical procedures, diagnostics and therapy has been significantly improved over recent years due to large studies and streamlined data analysis.

Such increased availability (and amounts) of data that may be useful for defining resource utilization and/or workflow increases the complexity and processing requirements of resource allocation processes. This can make it impossible, or at least very difficult, to provide optimized resource utilization and/or workflow to specific subjects. As a result, existing approaches typically aim to optimize the resource utilization and/or workflow for various "average" or "typical" subjects. This, however, is problematic where there are lower numbers of "average" subjects. Such approaches also have the drawback that every "non-average" subject disturbs the optimal workflow that has been specifically generated with an average subject in mind.

With optimal resource utilization and/or workflow being of paramount importance, especially in respect of medical/clinical resources, there remains a need for an approach to matching a subject to resources and tailoring the workflow accordingly.

SUMMARY OF THE INVENTION

The invention aims to at least partly fulfil the aforementioned needs. To this end, the invention provides devices, systems and methods as defined in the independent claims. The dependent claims provide advantageous embodiments.

There is provided a method for matching a subject to one or more resources. The method comprises obtaining data associated with a subject, the data comprising, for each of a plurality of parameters, a parameter value relating to the subject. The method further comprises generating a plurality of data groups for characterising the subject, each data group comprising parameter values relating to the subject for a subset of the plurality of parameters. The method further comprises applying a classification process to each data group of the plurality of data groups to identify a class value within a predetermined set or range of available values for each data group. The subject is then matched to one or more resources or workflow steps based on the identified class values.

The step of applying a classification process to each data group comprises, for each data group: determining a measure of population of the data group; and, based on the determined measure of population of the data group, applying at least one of a plurality of classification processes to the data group to identify a class value within a predetermined set or range of available for the data group. Thus, depending on the 'filling' of a data group, different classification methods may be employed. For example, if a data group is sparsely filled (e.g. there is insufficient data to robustly apply a conventional clustering technique, such as k-means clustering algorithm for example), a rule-based classification approach may be employed. Conversely, if a data group is sufficiently-filled, one or more machine learning algorithms (e.g. k-means, SVM) may be employed.

Proposed is a concept of splitting data associated with a subject (such as a person or patient) into different groups which enables the number of parameters within a respective group (or 'parameter space') to be reduced or kept low (relative to a number of data samples, measurements, subjects, etc.) so as to facilitate statistical classification of the groups. Unlike conventional approaches of clustering and classifying data (which typically take all parameters into one group or space and then try to perform clustering over all parameters at once), proposed embodiments take a contrary approach by creating sub-groups (or sub-spaces) relating to different subsets of parameters. This approach can help to ensure that each group/space is highly populated with data so as to improve data clustering reliability (which may depend on a sufficient number of data samples being available to learn parameter dependencies for example). A concept is thus proposed which is contrary to some conventional deep-learning approaches which "throw everything together" and rely on a large number of samples to identify parameter dependencies.

Thus, there is proposed an approach to analysing data relating to a subject and using the analysis result(s) to match the subject to one or more resources or tailored workflow steps, thereby improving resource usage in terms of efficiency, costs, customization, best practice for a subject, etc. Such a proposed approach includes splitting parameters/features for describing subjects into ensembles/groups characterizing the subject at different levels/scales (e.g. a subject may be characterised using groups relating to: "elderly patient", "disabled patient", "claustrophobic patient", "initial check-up", "MRI", "regional hospital"). Classification of data relating to a subject may then be performed for each group, thereby enabling classification of the subject with respect to each group. In this way, classification can be performed in multiple, smaller parameter groups/spaces. Results of the classifications may then be employed to match the subject to one or more resources in an optimal or preferred manner.

Embodiments may therefore enable a subject to be matched to resources so that resource utilization and/or workflow can be tailored to specific characteristics of the subject.

Also, resource usage based on an earlier classification and resource-matching process may be monitored and/or detected so as to provide feedback information which can be used to refine or improve subsequent classification and resource-matching processes.

In particular, embodiments may be used in relation a patient (as the subject) and clinical or medical resources so as optimize allocation or use of the clinical or medical resources for the specific subject. Such embodiments may support clinical planning. Improved Clinical Decision Support (CDS) may therefore be provided by proposed concepts.

Also, the collection and analysis of comprehensive subject data may facilitate correlation of subject and disease-specific characteristics, which may, in turn, be used for subject-specific or tailored diagnostics. The same holds for data relating to medical equipment and its efficient use. Proposed approaches may focus on the combination of data relating to a subject (e.g. patient) and data relating to the resource(s) (e.g. medical/clinical equipment) to enable efficient and flexible resource usage (e.g. diagnostics). By way of example, this may provide for: reduced subject administration or interrogation; improved subject comfort; increased subject throughput; creation of best practice diagnostic procedures; and iterative improvement of subject/disease-specific diagnostics. Embodiments may therefore enable value optimization of diagnostic processes and workflow through subject, disease and setting specific data analytics.

For instance, the proposed approach follows a scaled communicating clusters approach with an adaptive granularity in these clusters. So, instead of assuming that data relating to a subject and one or more resources can be grouped into larger (homogeneous) ensembles throughout, it is assumed, that the granularity on the finest scale is a subject with particular parameter values and a subject-specific workflow for certain resources. This subject is, however, connected to larger clusters on coarser scales, e.g. data groups having a respective set of parameters. Classification processes may be used on the finer scales and data analysis approaches can be used on the coarser scales while maintaining a very specific, i.e. subject-specific procedure at the patient level.

Accordingly, concepts are proposed which may match resources (such a medical equipment or clinical resources) to a particular subject (e.g. patient or individual user). This may enable the resource usage to be tailored and/or optimized for an individual subject.

Advantages associated with proposed embodiments may therefore include: (a) optimization of resource usage or allocation without software engineering efforts; and (b) increased value of available information through the use of insights from data analytics and available data to identify and differentiate parameters for characterising a subject.

In some embodiments, applying one of a plurality of classification processes to the data group may comprise: comparing the determined measure of population of the data group with a predetermined threshold; and, based on the result of the comparison, applying either a machine-learning based clustering process or a rule-based clustering process to the data group.

To determine the threshold, e.g. the cut-off point between a sufficiently-filled group or a sparsely-filled group, different approaches may be used. For example, one approach may be based on the knowledge that, for some clustering tasks, one may know a-priory that the data group is so large that there will not be enough data to fill the space (e.g. trying to derive the optimal value for all parameters of an optimal Magnetic Resonance Imaging (MRI) sequence by looking at clustering over the space of: initial diagnosis, rating of the recorded MRI image and all MRI sequence parameters). If that is the case a rule or look-up-table based clustering should be preferred. However, if it is not clear a-priori if there is enough data, one may look for classification stability by leaving a certain percentage of samples out and checking if the classification result is still the same. If it is not the same, i.e. the classification result is not stable, the data may not be sufficient for a reliable "conventional" clustering.

When the data groups are not known beforehand, it may be preferable to employ a machine-learning process (such as a k-means algorithm). Conversely, when the data groups are known, it may be preferable to employ a supervised learning method. Accordingly, over the lifetime of a proposed embodiment, one may begin with unsupervised classification processes and when enough data and knowledge has been gathered, one may switch to employing some supervised classification processes.

A classification value for a data group comprises a value within a predetermined set or range of available values. For example, the identification may comprise a numerical value, such as a number between 0-1 or 0%-100% for example. In this way, a characteristics of a subject (such as a "degree of patient mobility" for example) may be classified and represented using an identifier that is easy to understand and/or or simple to implement in conjunction with a matching process.

Each data group may comprise parameter values relating to the subject for a different subset of the plurality of parameters, each different subset of the plurality of parameters relating to a respective characteristic of the subject. For instance, each group may comprise data for a unique set of parameters which may be used to represent a particular characteristic of the subject. In this way, a first data group may comprise parameter values relating to the subject for a first subset of the plurality of parameters, and a second data group may comprise parameter values relating to the subject for a second, different subset of the plurality of parameters. Embodiments may therefore use insights from data analytics and available data to identify and differentiate data for identifying or specifying different characteristics of the subject.

The step of matching the subject to one or more resources based on the classification results (i.e. identified class values) may comprise: generating, based on the classification results, at least one of: a workflow for defining timing of resource usage; subject-specific instructions associated with one or more resources; and a sequence for defining an order of resource usage. For example, a resulting class value which represents a level of mobility may be translated into a required timeslot duration for a medical/clinical resource, thus relating the classification of the level of mobility to a required duration of resource usage. This translation of a level of mobility to duration may, for example, be based on prior knowledge/experience. However, this process of matching based on the classification results (e.g. translating level of mobility to duration) may be iteratively refined by feeding back observations on the resource usage (e.g. the duration of resource usage actually required as recorded by the medical device or scheduling software) into the matching (e.g. translation) algorithm.

Matching the subject to one or more resources may be further based on resource data relating to the one or more resources. For example, the resource data may comprise information relating to at least one of: availability; properties; characteristics; capabilities; and quantity of the one or more resources. This may enable the matching process to provide more accurate or efficient resource allocation by account for factors relating to the resource(s) that may influence optimal recourse allocation.

Embodiments may further comprise: obtaining usage data relating to use of the one or more resources by the subject; and modifying the classification process based on the obtained usage data. In this way, feedback may be used to modify or refine the classification process for improved accuracy and/or efficiency of resource matching. Thus, an iterative process of refining the classification and/or matching steps may be employed using observations on actual resource usage.

The subject may be a patient, and the one or more resources may comprise medical equipment. Embodiments may therefore be of particular benefit for medical or clinical applications where the allocation of medical/clinical resources to patients may be important. For instance, proposed embodiments may define resource workflows that are tailored or optimized for a specific individual or subject. This may, for example, provide numerous benefits including: reduction in subject administration and repetitive interrogation overhead; improvement in subject comfort, increased resource throughput, usage and quality; facilitate the creation of consistent best practice for diagnosis processes; and enable iterative improvement of subject/disease specific resource usage.

According to another aspect of the invention, there may be provided a computer program product for matching a subject to one or more resources, wherein the computer program product comprises a computer-readable storage medium having computer-readable program code embodied therewith, the computer-readable program code configured to perform all of the steps of a method according to a proposed embodiment.

According to another aspect of the invention, there is provided a system for matching a subject to one or more resources or workflow steps. The system comprises: an input interface adapted to obtain data associated with a subject, the data comprising, for each of a plurality of parameters, a parameter value relating to the subject; a data grouping unit adapted to generate a plurality of data groups for characterising the subject, each data group comprising parameter values relating to the subject for a subset of the plurality of parameters; a classification unit adapted to apply a classification process to each data group of the plurality of data groups to identify a class value within a predetermined set or range of available values for each data group; and a processing module adapted to match the subject to one or more resources or workflow steps based on the identified class values.

The classification unit is further adapted for each data group: to determine a measure of population of the data group; and, based on the determined measure of population of the data group, to apply at least one of a plurality of classification processes to the data group to identify a class value within a predetermined set or range of available for the data group.

In some embodiments, the processing module may be adapted to generate, based on the identified class values, at least one of: a workflow for defining timing of resource usage; subject-specific instructions associated with one or more resources; and a sequence for defining an order of resource usage.

Some embodiments may further comprises a feedback unit adapted to obtaining usage data relating to use of the one or more resources by the subject; and to modify the classification process based on the obtained usage data.

According to yet another aspect of the invention, there is provided a system for displaying resource-matching information relating to a matching of a subject to one or more resources. The system comprises: a system for matching a subject to one or more resources according to a proposed embodiment; a signal interface adapted to receive an input signal representative of data associated with the subject; an output interface adapted to generate a control signal for displaying resource-matching information; and a display unit adapted to display the resource-matching information in accordance with the generated control signal.

The processing module may be remotely located from the display unit, and the control signal may thus be communicated to the display unit via a communication link. In this way, a user (such as a resource administrator) may have an appropriately arranged display system that can receive and display resource-matching information at a location remotely located from the processing module. Embodiments may therefore enable a user to remotely review resource-matching information using a portable display device, such as a laptop, tablet computer, mobile phone, PDA, etc.

The system may further comprise: a server device comprising the data processing module; and a client device comprising the display unit. Dedicated data processing means may therefore be employed for the purpose of generating a subject-specific resource-matching information, thus reducing processing requirements or capabilities of other components or devices of the system.

The system may further comprise a client device, wherein the client device comprises the processing module and the display unit. In other words, a user (such as a resource administrator or medical professional) may have an appropriately arranged client device (such as a laptop, tablet computer, mobile phone, PDA, etc.) which processes received data in order to generate subject-specific resource-matching information and generate a control signal.

Thus, it will be understood that processing capabilities may therefore be distributed throughout the system in different ways according to predetermined constraints and/or availability of processing resources.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying schematic drawings, in which.

DETAILED DESCRIPTION OF THE EMBODIMENTS

Figure 1:
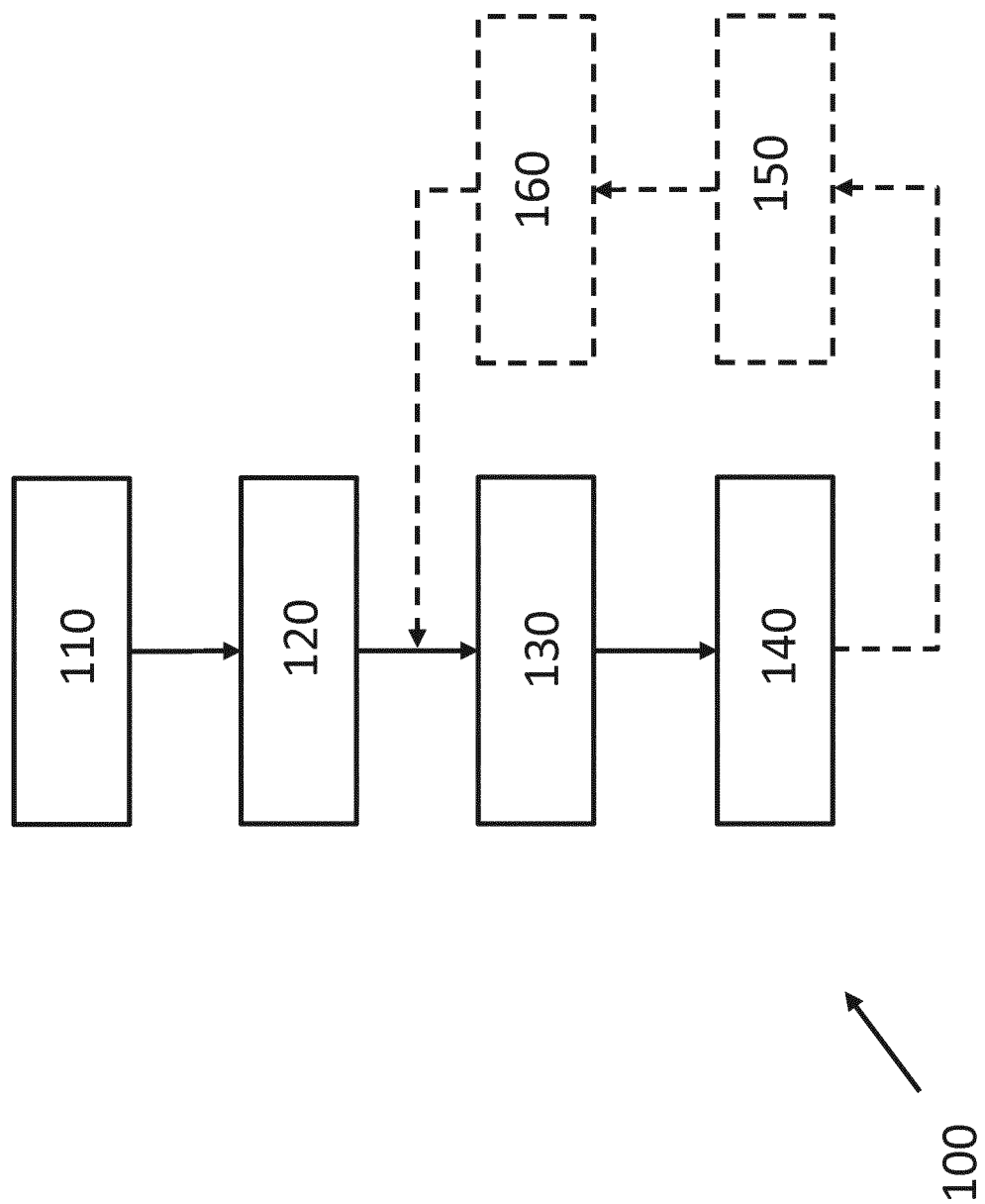
FIG. 1 is an exemplary flow diagram of a method for matching a subject to one or more resources according to an embodiment.

Proposed is a concept for matching a subject to one or more resources or workflow steps based on specific characteristics of the subject. Data comprising parameter values relating to the subject is split into data groups, wherein each data group comprises parameter values for a respective set of parameters. A classification process is applied to each data group so as to generate a classification result for each data group and the subject is then matched to one or more resources based on the classification results. By splitting data associated with a subject (such as a person or patient) into different groups, the number of parameters used in a respective group is reduced so as to facilitate statistical classification of the groups. Proposed embodiments employ an approach of creating or sub-spaces of data relating to different sets of parameters. This is contrary to conventional approaches to clustering and classifying data which typically use all parameters in a combined or total available space and then try to perform clustering over all parameters at once.

The proposed approach can help to ensure that each data group is highly populated with data so as to improve data clustering and classification reliability.

Embodiments may thus enable a single subject (such as a patient or individual) to be matched to resources (such as medical/clinical equipment or facilities) so that resource utilization and/or workflow is tailored to specific characteristics of the subject. For instance, where the subject is a patient, proposed concepts may optimize allocation or use of the clinical or medical resources for the subject. Improved clinical planning and resource allocation may therefore be provided according to specific characteristics of individual subjects.

Embodiments of the present invention are therefore directed toward enabling subject-specific clinical resource allocation so as to facilitate or enhance a CDS process. Further, embodiments may be aimed at enabling the provision of subject-specific workflows that make use of resources in an optimal manner.

Embodiments are based on the insight that, instead of assuming that data relating to a subject and one or more resources can be grouped into larger (homogeneous) ensembles throughout, the granularity on the finest scale is a subject with particular parameter values that may be used to define a subject-specific workflow and/or resource allocation. However, it is also realised that the subject may be connected to larger clusters on coarser scales, e.g. data groups having a respective set of parameters. To account for this, classification processes may be used on the finer scales and then data analysis approaches can be used on the coarser scales while maintaining a very specific, i.e. subject-specific procedure at the patient level.

Some proposed embodiments may therefore be thought of as splitting a plurality of parameters into ensembles/groups characterizing a subject at different levels and/or in different ways, and then performing classification of each of the parameter ensembles/groups. Once the various characteristics of a subject have been classified, the classification results can then be used to match the subject to one or more resources.

By way of example only, illustrative embodiments may be utilized in many different types of clinical, medical or patient-related environments, such as a hospital, doctor's office, ward, care home, person's home, etc. In order to provide a context for the description of elements and functionality of the illustrative embodiments, the Figures are provided hereafter as examples of how aspects of the illustrative embodiments may be implemented. However, it should be appreciated the Figures are only examples and are not intended to assert or imply any limitation with regard to the environments, systems or methods in which aspects or embodiments of the present invention may be implemented. For example, embodiments may not be limited to matching a subject to medical resources, but may instead be used in conjunction with other types or forms of subjects and resources.

Referring now to FIG. 1, there is depicted an exemplary flow diagram of a method 100 for matching a subject to one or more resources according to an embodiment. Here, the subject is a patient (i.e. a person receiving or registered to receive medical treatment) and wherein the one or more resources comprise medical or clinical resources (such a medical equipment, medical facilities, treatment programs and medical staff/professionals, for example).

The method begins in step 110 wherein data associated with a subject is obtained. The obtained data comprises parameter values relating to the subject for a plurality of parameters. For instance, the subject may be described using one hundred (100) different parameters that are each to describe a respective property or characteristic of the subject. Such parameters may, for example, include things like: age; weight; height; sex; hair colour; shoe size; alcohol intake; exercise frequency; pre-existing condition(s); etc. A parameter value relating to the subject for a parameter may thus represent a detected or obtained value of the parameter for that subject. A parameter value may thus comprise a numerical value, alphanumerical value, text value, colour, and other suitable identifier of value.

Next, in step 120, a plurality of data groups for characterising the subject is generated. Each data group comprises parameter values relating to the subject for a subset of the plurality of parameters. More specifically, in this example embodiment, each data group comprises parameter values relating to the subject for a different subset of the plurality of parameters. For instance, first and second data groups are created from the obtained data, wherein the first data group is representative of mobility and the second data group is representative of claustrophobia. The first group comprises parameter values for parameters relating to mobility, such as age, weight, invalidity and pre-existing condition(s). The second group comprises parameter values for a different set of parameters related to claustrophobia, such as age, pre-existing condition(s), and inquired/known degree of general claustrophobia. Thus, a number of data groups each representing a characteristic of the subject is formed. Such data groups may otherwise be thought of as 'parameter spaces' since they are each associated with a different set of parameters and thus form data spaces having a related set of parameters.

The method then proceeds to step 130 which comprises applying a classification process to each data group so as to generate a classification result for each data group. Here, a classification result for a data group comprises an identification of class membership or value within a predetermined set/range of available classes or values. By way of example, the identification of class or value comprises a numerical value, such as a number between 0-1 or 1%-100%. It will therefore be understood that the identification of class or value is adapted to represent or describe a value of characteristic of subject, and may thus comprise a numerical value, alphanumerical value, text value, colour, and other suitable identifier of value. Thus, considering this example wherein the first and second groups have been formed by step 120, completion of step 130 generates a classification value for each of the first and second groups. For instance, the classification value for the first group is representative of the degree of mobility for the subject and may comprise a value between 0 and 1, wherein 1 represents a highest level of mobility and 0 represents a lowest level of mobility (i.e. zero mobility). Similarly, the classification value for the second group is representative of the degree of claustrophobia for the subject and may comprise one of five available descriptive values, e.g. minimum, low, medium, high, or maximum.

In this way, characteristic of the subject can be classified and represented using an identifier that is easy to understand and/or or simple to implement in conjunction with a matching process.

In the example embodiment of FIG. 1, the step 130 of applying a classification process to each data group comprises, for each data group: determining a measure of population of the data group; and, based on the determined measure of population of the data group, applying at least one of a plurality of classification processes to the data group. Thus, depending on the 'filling' of a data group, different classification methods are employed. More specifically, if a data group is sparsely filled (e.g. there is insufficient data to robustly apply a conventional clustering technique, such as k-means clustering algorithm for example), a rule-based classification approach is employed. Conversely, if a data group is sufficiently-filled, one or more machine learning algorithms (e.g. k-means, SVM) may be employed. Thus, in step 130, applying one of a plurality of classification processes to a data group comprises the sub-steps of: comparing the determined measure of population of the data group with a predetermined threshold; and, based on the result of the comparison, applying either a machine-learning based clustering process or a rule-based clustering process to the data group.

Here, the threshold, e.g. the cut-off point between a sufficiently-filled group or a sparsely-filled group, is predetermined based on an assessment of classification stability by leaving a certain percentage of samples out and checking if the classification result is still the same. If it is not the same, the data may not be sufficient for a reliable "conventional" clustering.

The method then proceeds to step 140 of matching the subject to one or more resources based on the classification results. Here, matching the subject to one or more resources based on the classification results comprises: generating, based on the classification results, at least one of: a workflow for defining timing of resource usage; subject-specific instructions associated with one or more resources; and a sequence for defining an order of resource usage. For example, a resulting classification for the first group which represents a level of mobility is translated into a required timeslot duration for a medical/clinical resource, thus relating the classification of the level of mobility of the subject to a required duration of resource usage. This translation of a level of mobility to duration may, for example, be based on prior knowledge/experience. Similarly, a resulting classification for the second group which represents a level of claustrophobia is translated into a minimum required size of medical equipment (such as an MRI device) and/or subject notes/guidance to be associated with a medical/clinical resource, thus relating the classification of the level of claustrophobia of the subject to a resource size constraint and/or resource usage guidance. This translation may, again, be based on prior knowledge/experience.

Although not done so in the above-described example of FIG. 1, it is noted that the step 140 of matching the subject to one or more resources may also be further based on resource data relating to the one or more resources. Such resource data may, for example, comprise information relating to at least one of: availability; properties; characteristics; capabilities; and quantity of the one or more resources. This can potentially enable the matching process to provide more accurate or efficient resource allocation by account for factors relating to the resource(s) that may influence optimal recourse allocation.

Further to the method described above, it is noted that, after completion of step 140, resource usage (e.g. that prescribed based on the classification and resource-matching process of steps 110 through 140) may be monitored and/or detected so as to provide feedback information which can be used to refine or improve subsequent classification and resource-matching processes. Such an additional process is depicted in FIG. 1 by the dashed boxes and arrows. Accordingly, some embodiments may comprise the additional steps 150 and 160.

In step 150, the method obtains usage data relating to use of the one or more resources by the subject, and step 160 then comprises modifying the classification process based on the obtained usage data. In this way, feedback may be used to modify or refine the classification process for improved accuracy and/or efficiency of resource matching. Thus, an iterative process of refining the classification and/or matching steps may be employed using observations on (or measurements of) actual resource usage.

From the above-described methods, it will be a large number (e.g. many hundreds) of parameters relating to a subject (e.g. available from different databases/sources) may be split into ensembles/groups each characterizing the subject in a different way and/or at different levels/scales. For example, groups may be defined for characterising the following characteristics of a subject: "elderly patient", "disabled patient", "claustrophobic patient", "initial check-up", "MRI", and "regional hospital". In this way, classification can be performed in multiple smaller data groups (i.e. parameter spaces). As already mentioned above, depending on the filling of data groups, different classification methods can be employed.

An example of a proposed embodiment will now be described with reference to FIG. 2, wherein the subject is a patient.

Firstly, first 210 to fourth 240 data groups are defined. Using data from various sources (including a database of subject records 250, a disease database 260, an equipment performance database 270, an equipment schedule 275, and a hospital equipment database 277).

Here, the first group 210 is adapted to be representative of subject mobility and is thus associated with the following parameters: age; degree of invalidity; mobility related reason for stay/visit (e.g. surgery, accident with type). Accordingly, data is taken from the database of subject records 250, a disease database 260 and used to populate the first group 210 (as depicted by the arrows associated with the first group 210).

The second group 220 is adapted to be representative of subject claustrophobia and is thus associated with the following parameters: success rate of previous procedures (e.g. number of repetitions for previous MR-exams); age; and inquired/known psychological disorders. Accordingly, data is taken from the database of subject records 250, a disease database 260 and used to populate the second group 220 (as depicted by the arrows associated with the second group 220).

The third group 230 is adapted to be representative of subject's required imaging bore size (for an MRI device) and is thus associated with the following parameters: subject weight; degree of claustrophobia; and system availability/bore size. Accordingly, data is taken from the database of subject records 250, disease database 260 and equipment performance database 270 and used to populate the third group 230 (as depicted by the arrows associated with the third group 230).

The fourth group 240 is adapted to be representative of a subject's required imaging sequence and is thus associated with the following parameters: suitability for diagnostic question; duration of sequence; loudness of sequence; and feasibility depending on system type. Accordingly, data is taken from the disease database 260 and equipment performance database 270 and used to populate the fourth group 240 (as depicted by the arrows associated with the fourth group 240).

Here, it is noted that some parameters are "translated" and weighted by respective databases, e.g. the subject's psychological disorders are looked-up in the disease database 260 (where the corresponding "degree of claustrophobia" data is stored) and used as parameter for classification of the claustrophobia.

Next, classification of each group is performed. In this regard, the type of classification algorithm employed depends on how well a group is filled/populated. For instance, k-means clustering, support vector machines or genetic algorithms are used for sufficiently filled parameter spaces (e.g. the first 210 to third 230 data groups) and clinical guidelines/hard-coded rules are used for classifying the sparsely-filled parameter spaces (e.g. the fourth data group 240).

The classification results for each group are then provided to various data processing units (or 'engines') so as to match the subject to the resource(s). More specifically, engines may be summarised as follows:

(i) Workflow Engine 280: this translates the degree of subject mobility into a required duration for an imaging slot, and translates the required bore size into a specific system/device at the hospital, e.g. 1 hour slot at wide-bore system B;

(ii) Subject Experience Engine 290: this translate the degree of claustrophobia into special instructions to be followed by nurse/medical technologist, e.g. show preparatory video about imaging procedure during waiting (iii) Sequence Engine 300: this translates the required imaging sequence into specific sequence settings for a particular system.

Figure 2:
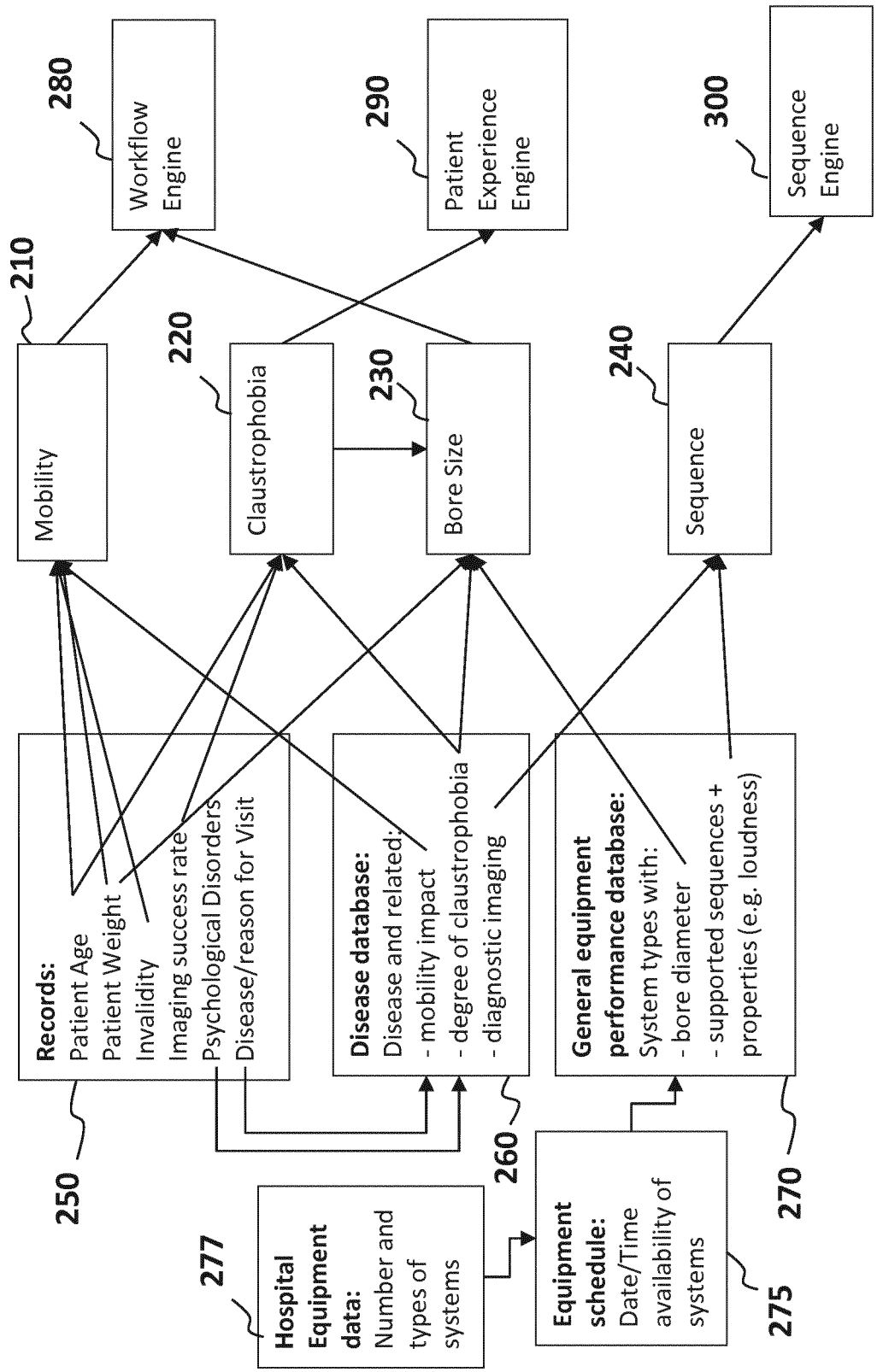
FIG. 2 is an illustration summarising a flow of information in a proposed embodiment.

The proposed embodiment illustrated by FIG. 2 is also adapted to record imaging workflow parameters, e.g. number of repetitions of images, and update parameter spaces, and then used this information to iteratively improve the classification processes.

Considering the example described above with reference to FIG. 2, and by way of aiding further understanding of the proposed concepts, a specific implementation example will now be considered in relation to four subjects, wherein the four subjects are denoted Subject 1, Subject 2, Subject 3 and Subject 4, respectively.

Table 1 below details parameter values for each of the four subjects:

TABLE 1

| Parameter | Subject 1 | Subject 2 | Subject 3 | Subject 4 |
|---|---|---|---|---|
| Age | 6 | 16 | 45 | 76 |
| Weight | 15 | 50 | 80 | 100 |
| Invalidity | 0.0 | 0.0 | 0.2 | 0.9 |
| MR repetition probability | 0.3 | 0.0 | 0.1 | 0.3 |
| psych. Disorders | 0.0 | 0.1 | 0.3 | 0.8 |
| Urgency | 0.8 | 1.0 | 0.3 | 0.5 |

A first group representative of subject mobility is then identified and associated with the parameters 'age' and 'invalidity'. More specifically, the association is defined such that a measure of mobility is represented by the following equation (Equation 1):

$$\text{Mobility} = (1 - 0.0004 \times (\text{Age} - 50)^2) \times (1 - \text{Invalidity}) \quad (1)$$

A second group representative of subject claustrophobia is also identified and associated with the parameters 'age', 'MR repetition probability' and 'psych. Disorders'. More specifically, the association is defined such that a measure of subject claustrophobia is represented by the following equation (Equation 2):

$$\text{MR Claustrophobia} = \text{MR repetition probability} \times \text{psych.Disorders} \times (0.0004 \times (\text{Age} - 50)^2) \quad (2)$$

A third group representative of required imaging bore size (for an MRI device) is also identified and associated with the parameters 'age', 'MR Claustrophobia' and Max. Weight (where Max. Weight for this example has an independently defined parameter value, such as 200 for example). More specifically, the association is defined such that a measure of required imaging bore size is represented by the following equation (Equation 3):

$$\text{Required Imaging Bore Size} = \text{MR Claustrophobia} \times \text{Weight}/\text{Max.Weight} \quad (3)$$

Based on the group definitions and the parameter values for the four subject, the four subjects are then classified as detailed in Table 2 below:

TABLE 2

| Parameter | Subject 1 | Subject 2 | Subject 3 | Subject 4 |
|---|---|---|---|---|
| "Mobility" | 0.223344 | 0.532224 | 0.792 | 0.07296 |
| "MR Claustrophobia" | 0.0023232 | 0.0004624 | 0.0003 | 0.064896 |
| Imaging bore size | 0.00017424 | 0.0001156 | 0.00012 | 0.032448 |

The above classification results can then be used to match the subjects to resources. For instance, where available MRI devices have associated imaging bore sizes that place a constraint on the size of subject, the MRI devices may for example be such that: a first ("open") MRI device caters for Imaging Bore Size values greater than 0.02; a second ("wide") MRI device caters for Imaging Bore Size values less than 0.02; and a third ("normal") MRI device caters for Imaging Bore Size values less than 0.0002. Comparison of the Imaging Bore Size value for each subject against such constraints then enables identification of which MRI devices can or cannot be used by each subject. For example, for the classification results detailed in Table 2 above, it can be concluded that Subject 4 can only be imaged using the first ("open") MRI device. This is because Subject 4 is classified as having an Imaging Bore Size of 0.032448 and only the first ("open") MRI device caters for Imaging Bore Size values greater than 0.02.

Here it is noted that conventional and widely known optimization algorithms from operational research (such as "travelling sales man problem", "job shop scheduling", "assignment problem", "linear programming", etc.) may be employed to match/assign the subject to resource while obeying predetermined resource constraints.

It will be appreciated that the above example may relate to 'device matching', wherein the resources allocated to the subjects comprise devices.

By way of further example, another implementation example will now be considered in relation to 'time slot matching', wherein the resources allocated comprise time slots (e.g. appointments). This example has the same four subjects (namely Subject 1, Subject 2, Subject 3 and Subject 4) as the preceding example. Table 3 below details parameter values for each of the four subjects that may be relevant for time slot matching.

TABLE 3

| Parameter | Subject 1 | Subject 2 | Subject 3 | Subject 4 |
|---|---|---|---|---|
| Age | 6 | 16 | 45 | 76 |
| Urgency | 1.0 | 100.0 | 30.0 | 30.0 |
| Scheduling Flexibility | 100.0 | 100.0 | 10.0 | 80.0 |
| Early Slot Preference | 1.0 | 1.0 | 20.0 | 50.0 |
| Middle Slot Preference | 1.0 | 50.0 | 1.0 | 100.0 |
| Late Slot Preference | 1.0 | 100.0 | 100.0 | 80.0 |

Here, the Urgency parameter is a diagnosis/record-based weight between 0 and 100, wherein a higher urgency value is representative of higher urgency (e.g. greater need to attend a timeslot as soon as possible). The Scheduling Flexibility parameter has values between 0 and 100, wherein lower values indicate a generally lower flexibility (e.g. reduced amount of free time and/or increased commitment to adhering to another schedule). The Early, Middle and Late Slot Preference parameters each have values between 0 and 100 and indicate a patient request/feedback-based slot preference. A value of zero for the Early, Middle and Late Slot Preference parameters indicates that no preference is available/given for a specific time slot.

A first group associated with an Early Slot is then defined and associated with the parameters 'Urgency', 'Scheduling Flexibility' and 'Early Slot Preference'. More specifically, the association is defined such that a measure of suitability for Early Slot is represented by the following equation (Equation 4):

$$\text{Early Slot Suitability} = 3*\text{Urgency} + (101 - \text{Scheduling Flexibility}) + \text{Early Slot Preference} \quad (4)$$

A second group associated with a Middle Slot is defined and associated with the parameters 'Urgency', 'Scheduling Flexibility' and 'Middle Slot Preference'. More specifically, the association is defined such that a measure of suitability for a Middle Slot is represented by the following equation (Equation 5):

$$\text{Middle Slot Suitability} = 2*\text{Urgency} + (101 - \text{Scheduling Flexibility}) + \text{Middle Slot Preference} \quad (5)$$

A third group associated with a Late Slot is defined and associated with the parameters 'Urgency', 'Scheduling Flexibility' and 'Late Slot Preference'. More specifically, the association is defined such that a measure of suitability for a Late Slot is represented by the following equation (Equation 6):

$$\text{Late Slot Suitability} = \text{Urgency} + (101 - \text{Scheduling Flexibility}) + \text{Late Slot Preference} \quad (5)$$

Based on the group definitions and the parameter values for the four subject, the four subjects are then classified as detailed in Table 4 below:

TABLE 4

| Parameter | Subject 1 | Subject 2 | Subject 3 | Subject 4 |
|---|---|---|---|---|
| Early Slot | 5 | 302 | 201 | 161 |
| Middle Slot | 4 | 251 | 152 | 181 |
| Late Slot | 3 | 201 | 221 | 131 |

The above results can then be used to match the subjects to time slots. For instance: Subject 2 (due to the high urgency) should be scheduled for an early slot (even though this does not fulfil his/her slot preference); Subject 3 can be scheduled for a late slot (due to lower urgency), thus fulfilling his/her preference and respecting the lower flexibility; Subject 4 should be scheduled for the middle slot (due to lower urgency), thus fulfilling his/her preference (with a lower matching result value due to the higher flexibility); and Subject 1 can be scheduled for any slot due to low urgency and high flexibility/no preference.

This example illustrates the scheduling engine aspect of the proposed method, but it may be combined with the parameter space of the preceding example (i.e. device matching), during the matching and optimization stage to achieve a final assignment result.

Here it is noted that conventional and widely known optimization algorithms from operational research (such as "travelling sales man problem", "job shop scheduling", "assignment problem", "linear programming", etc.) may be employed to match/assign the subject to resource while obeying predetermined resource constraints.

An exemplary implementation of a proposed embodiment will now be described with reference to FIG. 3. The example relates to using a specific subject workflow related to diagnostic imaging, but it will be appreciated that other embodiments can readily be extended to other applications.

Figure 3:
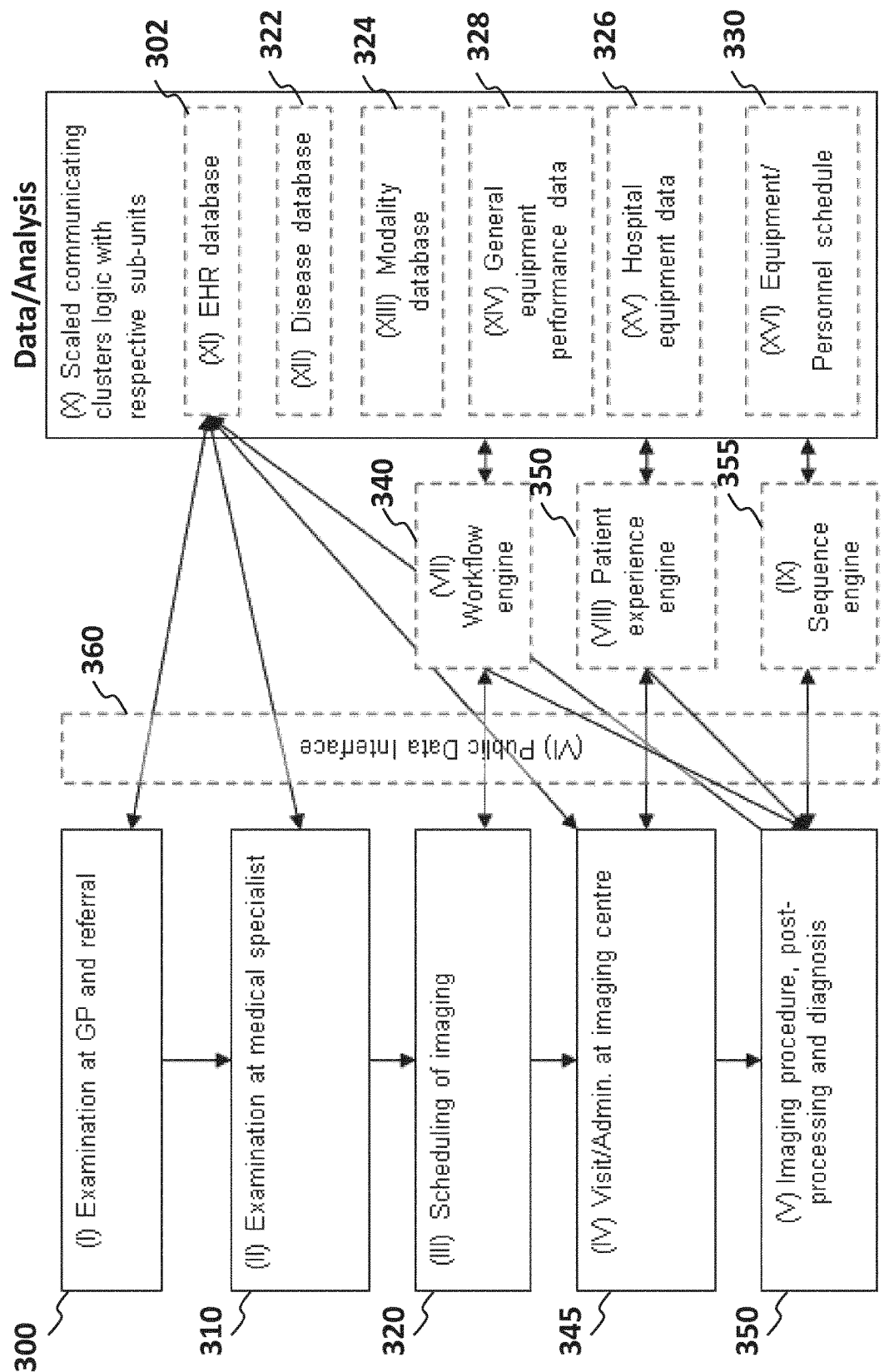
FIG. 3 is an illustration summarising an exemplary implementation of a proposed embodiment.

The boxes on the right side of FIG. 3, within the box labelled "Data/Analysis" represent the accumulated knowledge/data (e.g. databases) including their complex correlations and their numeric representation. These are built upon domain knowledge/rules (e.g. medical, technical, administrative, financial . . . ) and are iteratively extended by the feedback mechanism (indicated by arrows directed towards the "engines"). These "engines" represent algorithms which extract a subset of parameters for respective parts of the overall workflow.

The implementation begins with a subject examination 300 by a general practitioner (GP) with resulting referral to a medical specialist. This involves recording of subject specific information, e.g. age, gender, pre-existing conditions, allergies, which is then transferred to Examination of Health and Referral (EHR) database 302. Recording of information relevant for potentially upcoming examinations or medical procedures, e.g. claustrophobia, bad hearing, etc. may also be undertaken and transferred to the EHR database 302.

At the subsequent examination 310 by the medical specialist, further recording, updating, and addition of subject specific information is undertaken, and such information is and transferred to the EHR database 302. The examination 310 by the medical specialist may also comprise the structured recording of diagnostic information, e.g. suspected disease/grading and diagnostic question to be addressed by a prescribed imaging procedure, with the information then being transferred to the EHR database 302.

The next step, step 320, entails scheduling of the prescribed imaging procedure based on hospital logistics and subject/disease specific boundary conditions. This is undertaken based on data from the EHR database 302 (e.g. obese, claustrophobic subject, visual and walking impairment, preferably no appointment in the afternoon), a disease database 322 (e.g. diagnostic question and needed diagnostics according to guidelines), a modality database 324 (e.g. field strength dependent protocols and their duration for specific diagnostic questions/diseases), a hospital equipment database 326 (e.g. 1× Type 1 and 2× Type 2 MRI scanners available), a general equipment performance database 328 (e.g. Type 1 MRI scanner accommodates obese claustrophobic subjects better than Type 2 MRI scanner), and an equipment/personnel schedule 330 (e.g. normal working hours, reserved time slots). Based on such data, a weighted schedule with possible time slots for appointments information is created by the workflow engine 340. This information can be created using known clustering techniques (e.g. nearest neighbours) and distance measures/weights being stored for all relations in the respective database (e.g. appropriateness rating according to clinical guidelines for specific diseases). A specific timeslot is then selected by the subject, and the selected timeslot is recorded in a hospital schedule (e.g. wheelchair and assistance person needed at reception before the time slot starts).

During the selected timeslot, the subject visits 345 the imaging centre, wherein the subject is registered and confirmation of time-slot recorded in a scheduling system, (e.g. noting that the timeslot is definitely used otherwise standby subjects might advance). Using information from a subject experience engine 350, a receptionist and assistant can react accordingly (e.g. respond to subject's impairments). During the visit 345, additional subject information is recorded and transferred to the EHR database 302. The subject also receives subject specific information (based on the workflow and subject experience engine 350 output) and is directed/guided to the appropriate imaging resources.

During the imaging procedure 350, pre-computed general imaging setup (e.g. workflow) provided by the workflow engine 340 (e.g. needed contrasts, anatomical regions and resolution) is employed to customise the imaging procedure 350 to the specific subject. Also, specific sequence settings (e.g. taking into account subject size and claustrophobia) are provided by subject experience engine 350 and the sequence engine 355. After running the imaging sequence(s), the diagnostic results are transferred to the EHR database 302. Subject and/or personnel feedback is also transferred so as to re-adjust weights between input and output parameters if needed.

In the example of FIG. 3, the public data interface 360 serves as an abstraction layer for communication with the databases and dedicated engines as well as for enforcing access and security control.

Also, it is noted that the workflow engine 340 creates a (weighted list of) appointment(s) and a respective sequence of imaging procedures/protocols to be run during the imaging session. The weighted list is created using the scaled communicating clusters logic with respective sub-units. A principle of this approach is to "annotate" categorical input data with weighted links to the respective output and to create multiple layers of abstraction (e.g. oncology—abdomen—kind of cancer) which allow to scale the specificity of the input and output information and link the different levels with transition weights. It also derives the weighted output/results by clustering large amount of data (e.g. EHR records) with respect to relevant input data (e.g. subject information) and their assigned class (e.g. subject requiring special attention) by e.g. nearest neighbour classifiers, support vector machine etc.

Figure 4:
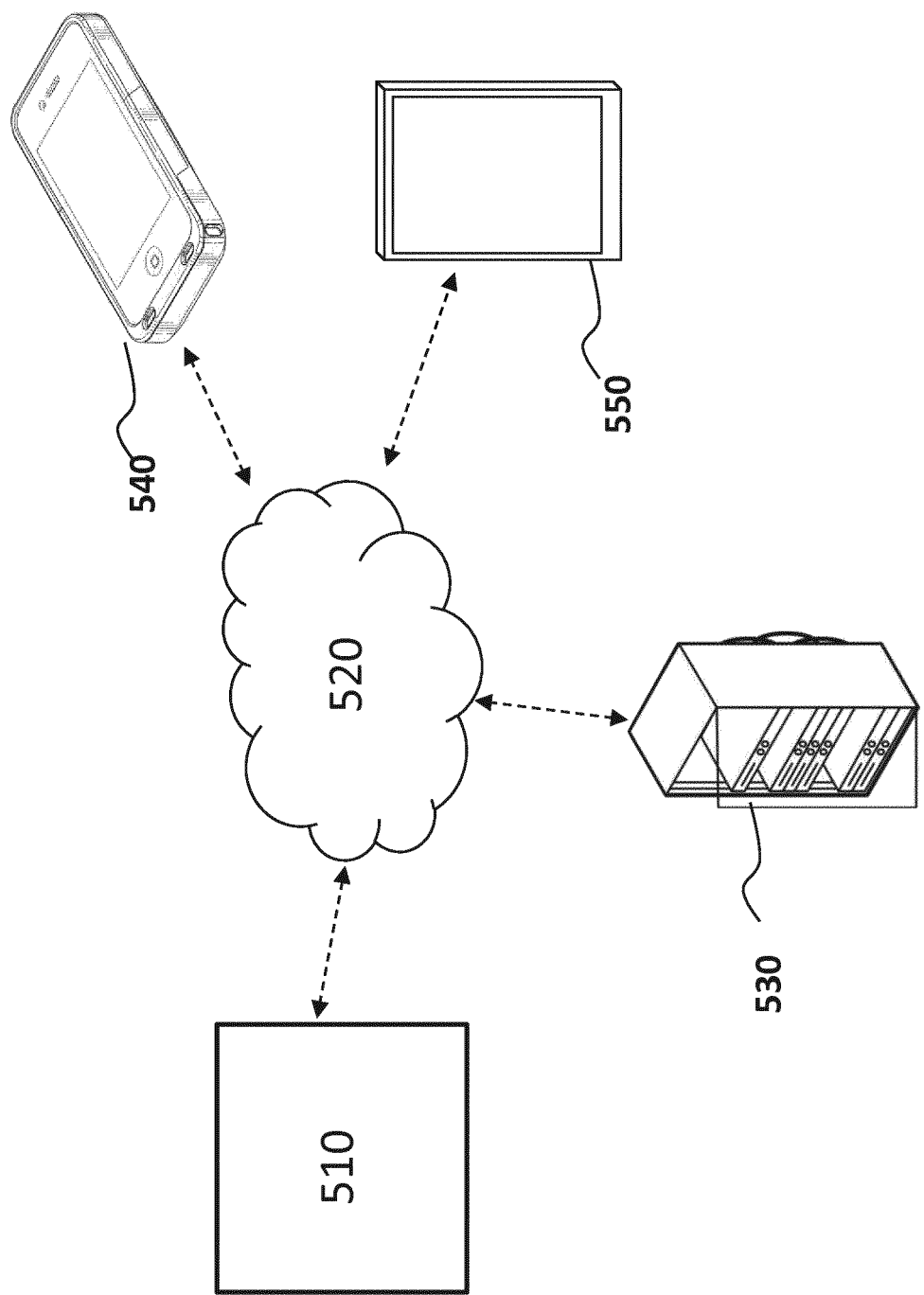
FIG. 4 is a simplified block diagram of a system according to an embodiment.

Referring now to FIG. 4, there is depicted an embodiment of a system according to an embodiment of the invention comprising an input system 510 arranged to obtain various sets of information Here, the input system 510 is adapted to obtain data associated with a subject, the obtained data comprising parameter values relating to the subject for a plurality of parameters. The input system 510 is adapted to output one or more signals which are representative of obtained information/data.

The input system 510 communicates the output signals via a network 520 (using a wired or wireless connection for example) to a remotely located data processing system 530 (such as server).

The data processing system 530 is adapted to receive the one or more output signals from the input system 510 and process the received signal(s) to generate a plurality of data groups for characterising the subject, wherein each data group comprises parameter values relating to the subject for a subset of the plurality of parameters. The data processing system 530 is also adapted to apply a classification process to each data group so as to generate a classification result for each data group. Based on the classification results, the data processing system matches the subject to available resources. Thus, the data processing 530 provides a centrally accessible processing resource that can receive information from the input system 510 and run one or more algorithms to transform the received information into a resource utilization definition and/or workflow that is tailored to specific characteristics of the subject. Information relating to the subject-specific resource utilization definition and/or workflow can be stored by the data processing system (for example, in a database) and provided to other components of the system. Such provision of information about a subject-specific resource utilization definition and/or workflow may be undertaken in response to a receiving a request (via the network 520 for example) and/or may be undertaken without request (i.e. 'pushed').

For the purpose of receiving information about a subject-specific resource utilization definition and/or workflow from the data processing system 530, and thus to enable subject-specific information to be viewed, the system further comprises first 540 and second 550 mobile computing devices.

Here, the first mobile computing device 540 is a mobile telephone device (such as a smartphone) with a display for displaying information in accordance with embodiments of the proposed concepts. The second mobile computing device 550 is a mobile computer such as a Laptop or Tablet computer with a display for displaying information in accordance with embodiments of the proposed concepts.

The data processing system 530 is adapted to communicate clinical model output signals to the first 540 and second 550 mobile computing devices via the network 520 (using a wired or wireless connection for example). As mentioned above, this may be undertaken in response to receiving a request from the first 540 or second 550 mobile computing devices.

Based on the received output signals, the first 540 and second 550 mobile computing devices are adapted to display one or more graphical elements in a display area provided by their respective display. For this purpose, the first 540 and second 550 mobile computing devices each comprise a software application for processing, decrypting and/or interpreting received output signals in order to determine how to display graphical elements. Thus, the first 540 and second 550 mobile computing devices each comprise a processing arrangement adapted to determine an attribute of a subject-specific resource utilization definition and/or workflow, and to generate a display control signal for modifying at least one of the size, shape, position, orientation, pulsation or colour of a graphical element based on the determined attribute of the subject-specific resource utilization definition and/or workflow.

The system can therefore communicate information about subject-specific resource utilization definitions and/or workflows to users of the first 540 and second 550 mobile computing devices. For example, each of the first 540 and second 550 mobile computing devices may be used to display graphical elements to a medical practitioner, doctor, consultant, technician or caregiver for example.

Figure 5:
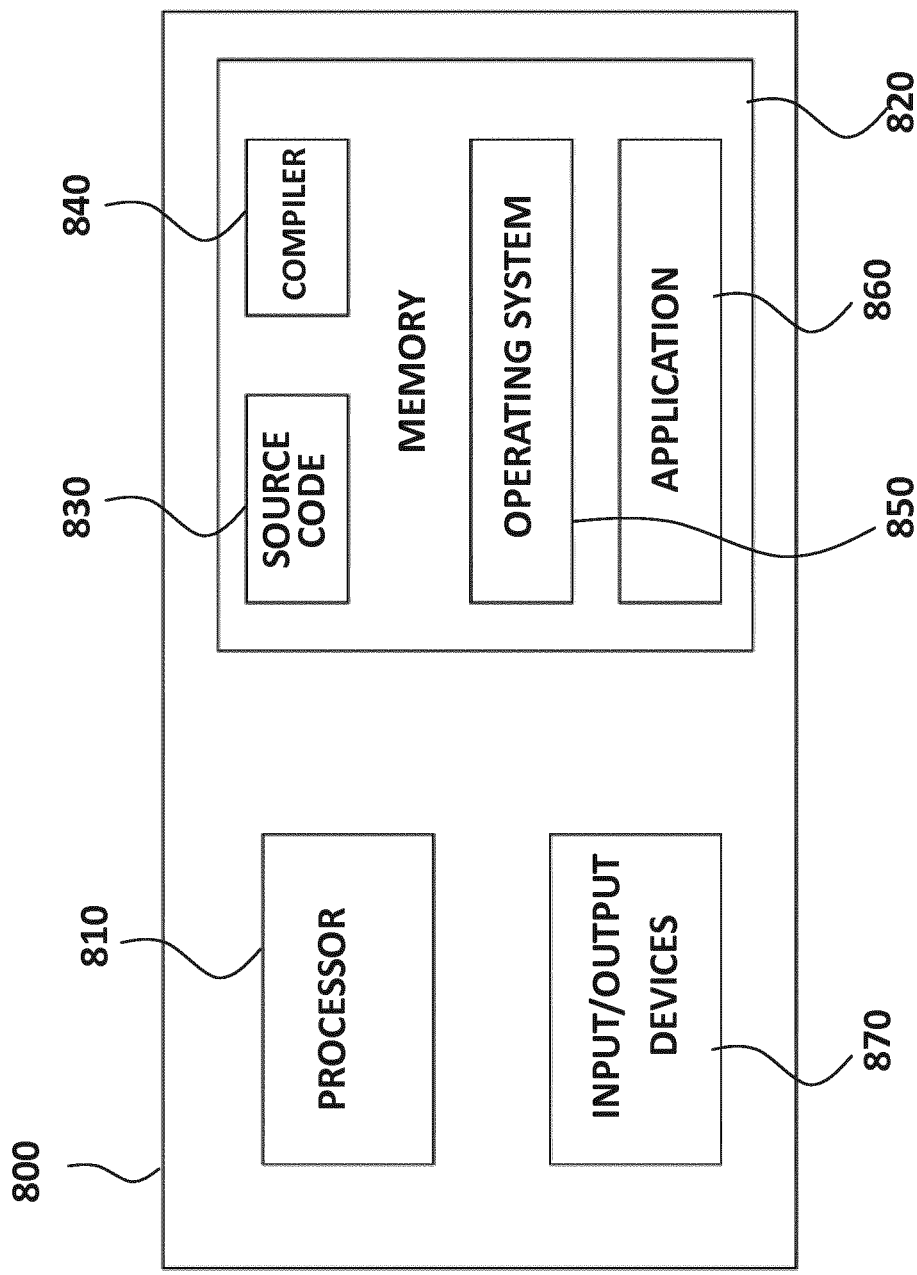
FIG. 5 is a simplified block diagram of a computer within which one or more parts of an embodiment may be employed.

Implementations of the system of FIG. 5 may vary between: (i) a situation where the data processing system 530 communicates display-ready data, which may for example comprise display data including graphical elements (e.g. in JPEG or other image formats) that are simply displayed to a user of a mobile computing device using conventional image or webpage display (can be web based browser etc.); to (ii) a situation where the data processing system 530 communicates raw data set information that the receiving mobile computing device then splits the data into data groups, applies a classification processes to each group to generate classification results, matches a subject to resources based on the classification results, and then displays graphical elements based on the determined matching (for example, using local software running on the mobile computing device). Of course, in other implementations, the processing may be shared between the data processing system 530 and a receiving mobile computing device such that data groups generated at data processing system 530 is sent to the mobile computing device for further processing by local dedicated software of the mobile computing device. Embodiments may therefore employ server-side processing, client-side processing, or any combination thereof.

Further, where the data processing system 530 does not 'push' information about a subject-specific resource utilization definition and/or workflow, but rather communicates information in response to receiving a request, the user of a device making such a request may be required to confirm or authenticate their identity and/or security credentials in order for information to be communicated.

FIG. 5 illustrates an example of a computer 800 within which one or more parts of an embodiment may be employed. Various operations discussed above may utilize the capabilities of the computer 800. For example, one or more parts of a system for providing subject-specific information (or display unit thereof) may be incorporated in any element, module, application, and/or component discussed herein.

The computer 800 includes, but is not limited to, PCs, workstations, laptops, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a microprocessor.

The memory 820 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. It is contemplated by the inventors that the application 860 for implementing exemplary embodiments may be applicable on all commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 870 may include input devices such as, for example but not limited to, a mouse, keyboard, scanner, microphone, camera, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 860 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand various embodiments with various modifications are contemplated.

The invention claimed is:

1. A computer-implemented method for matching a subject to one or more resources or workflow steps, the method comprising:
    obtaining data associated with a subject, the data comprising, for each of a plurality of parameters, a parameter value relating to the subject;
    generating a plurality of data groups for characterizing the subject, each data group comprising parameter values relating to the subject for a subset of the plurality of parameters;
    applying a classification process to each data group of the plurality of data groups to identify a class value within a predetermined set or range of available values for each data group;
    matching the subject to one or more resources or workflow steps based on the identified class values; and
    based on the identified class values, generating: a workflow for defining timing of resource usage; subject-specific instructions associated with one or more resources; and a sequence for defining an order of resource usage, wherein applying a classification process to each data group comprises, for each data group:
    determining a measure of population of the data group; and, based on the determined measure of population of the data group, applying at least one of a plurality of classification processes to the data group to identify a class value within a predetermined set or range available for the data group.

2. The method of claim 1, wherein applying one of a plurality of classification processes to the data group comprises: comparing the determined measure of population of the data group with a predetermined threshold; and, based on a result of the comparing, applying either a machine-learning based clustering process or a rule-based clustering process to the data group.

3. The method of claim 1, wherein the class value for a data group comprises a numerical value.

4. The method of claim 1, wherein each data group comprises parameter values relating to the subject for a different subset of the plurality of parameters, each different subset of the plurality of parameters relating to a respective characteristic of the subject.

5. The method of claim 1, wherein matching the subject to one or more resources is further based on resource data relating to the one or more resources.

6. The method of claim 5, wherein the resource data comprises information relating to at least one of: availability; properties; characteristics; capabilities; and quantity of the one or more resources.

7. The method of claim 1, further comprising:
    obtaining usage data relating to use of the one or more resources by the subject; and
    modifying the classification process based on the obtained usage data.

8. The method of claim 1, wherein the subject is a patient, and wherein the one or more resources comprise medical equipment.

9. A system for matching a subject to one or more resources or workflow steps, the system comprising:
    an input interface adapted to obtain data associated with a subject, the data comprising, for each of a plurality of parameters, a parameter value relating to the subject;
    a processor; and
    a memory that stores instructions, which when executed by the processor causes the processor to:
    generate a plurality of data groups for characterising the subject, each data group comprising parameter values relating to the subject for a subset of the plurality of parameters;
    apply a classification process to each data group of the plurality of data groups to identify a class value within a predetermined set or range of available values for each data group;
    for each data group, determine a measure of population of the data group; and, based on the determined measure of population of the data group, apply at least one of a plurality of classification processes to the data group to identify a class value within a predetermined set or range available for the data group;
    match the subject to one or more resources or workflow steps based on the identified class values; and
    based on the identified class values, generate: a workflow for defining timing of resource usage; subject-specific instructions associated with one or more resources; and a sequence for defining an order of resource usage.

10. The system of claim 9, wherein the instructions, when executed by the processor, further cause the processor to match the subject to one or more resources further based on resource data relating to the one or more resources.

11. The system of claim 9, wherein the instructions, when executed by the processor, further cause processor to obtain usage data relating to use of the one or more resources by the subject, and to modify the classification process based on the obtained usage data.

12. The system of claim 9, wherein the instructions, when executed by the processor, further cause the processor to:

obtain usage data relating to use of the one or more resources by the subject; and to modify the classification process based on the obtained usage data.

13. A tangible, non-transitory computer readable medium that stores instructions, which when executed by a processor, cause the processor to:
   obtain data associated with a subject, the data comprising, for each of a plurality of parameters, a parameter value relating to the subject;
   generate a plurality of data groups for characterizing the subject, each data group comprising parameter values relating to the subject for a subset of the plurality of parameters;
   apply a classification process to each data group of the plurality of data groups to identify a class value within a predetermined set or range of available values for each data group;
   match the subject to one or more resources or workflow steps based on the identified class values; and
   based on the identified class values, generate: a workflow for defining timing of resource usage; subject-specific instructions associated with one or more resources; and a sequence for defining an order of resource usage;
   wherein the application of the classification process to each data group comprises, for each data group causes the processor to: determine a measure of population of the data group; and, based on the determined measure of population of the data group, apply at least one of a plurality of classification processes to the data group to identify a class value within a predetermined set or range available for the data group.

14. The tangible, non-transitory computer readable medium of claim 13, wherein when executed by the processor, the instructions further cause the processor to compare the determined measure of population of the data group with a predetermined threshold; and, based on a result of the comparing, apply either a machine-learning based clustering process or a rule-based clustering process to the data group.

15. The tangible, non-transitory computer readable medium of claim 13, wherein the class value for a data group comprises a numerical value.

16. The tangible, non-transitory computer readable medium of claim 13, wherein each data group comprises parameter values relating to the subject for a different subset of the plurality of parameters, each different subset of the plurality of parameters relating to a respective characteristic of the subject.

17. The tangible, non-transitory computer readable medium of claim 13, wherein the match of the subject to one or more resources is further based on resource data relating to the one or more resources.

* * * * *